US00PP20598P2

(12) United States Plant Patent
Wood

(10) Patent No.: US PP20,598 P2
(45) Date of Patent: Dec. 22, 2009

(54) ***PHYSOCARPUS* PLANT NAMED 'TRES'**

(50) Latin Name: *Physocarpus opulifolius*
Varietal Denomination: Tres

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/287,354

(22) Filed: Oct. 8, 2008

(51) Int. Cl.
*A01H 5/00* (2006.01)

(52) U.S. Cl. ..... Plt./226

(58) Field of Classification Search ..... Plt./226

See application file for complete search history.

*Primary Examiner*—Kent L Bell
(74) *Attorney, Agent, or Firm*—C. A. Whealy

(57) ABSTRACT

A new and distinct cultivar of *Physocarpus* plant named 'Tres', characterized by its compact, upright and rounded plant habit; vigorous growth habit; freely branching habit; dense and bushy habit; dark burgundy-colored leaves; showy inflorescences with white-colored flowers; and good garden performance.

1 Drawing Sheet

Botanical designation: *Physocarpus opulifolius.*
Cultivar denomination: 'Tres'.

BACKGROUND OF THE INVENTION

The present invention relates to a new and distinct cultivar of *Physocarpus,* botanically known as *Physocarpus opulifolius* and hereinafter referred to by the name 'Tres'.

The new *Physocarpus* is a product of a controlled breeding program conducted by the Inventor in Grand Haven, Mich. The objective of the breeding program is to create new *Physocarpus* cultivars with unique foliage types.

The new *Physocarpus* plant originated from a cross-pollination in June, 2000 of *Physocarpus opulifolius* 'Nana', not patented, as the female, or seed, parent with *Physocarpus opulifolius* 'Monlo', disclosed in U.S. Plant Pat. No. 11,211, as the male, or pollen, parent. The new *Physocarpus* plant was discovered and selected by the Inventor in 2003 as a flowering plant within the progeny of the stated cross-pollination in a controlled environment in Grand Haven, Mich.

Asexual reproduction of the new *Physocarpus* plant by softwood cuttings in a controlled environment in Grand Haven, Mich. since the summer of 2003 has shown that the unique features of this new *Physocarpus* plant are stable and reproduced true to type in successive generations of asexual reproduction.

SUMMARY OF THE INVENTION

Plants of the new *Physocarpus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Tres'. These characteristics in combination distinguish 'Tres' as a new and distinct cultivar of *Physocarpus:*

1. Compact, upright and rounded plant habit.
2. Vigorous growth habit.
3. Freely branching habit; dense and bushy habit.

4. Dark burgundy-colored leaves.
5. Showy inflorescences with white-colored flowers.
6. Good garden performance.

Plants of the new *Physocarpus* can be compared to plants of the female parent, 'Nana'. Plants of the new *Physocarpus* differ from plants of 'Nana' in the following characteristics:

1. Plants of the new *Physocarpus* are not as compact as plants of 'Nana'.
2. Plants of the new *Physocarpus* are more upright than plants of 'Nana'.
3. Plants of the new *Physocarpus* and 'Nana' differ in leaf color as plants of 'Nana' have green-colored leaves.

Plants of the new *Physocarpus* can be compared to plants of the male parent, 'Monlo'. Plants of the new *Physocarpus* differ from plants of 'Monlo' in the following characteristics:

1. Plants of the new *Physocarpus* are much more compact than plants of 'Monlo'.
2. Plants of the new *Physocarpus* are more freely branching than plants of 'Monlo'.
3. Plants of the new *Physocarpus* have smaller leaves than plants of 'Monlo'.
4. Plants of the new *Physocarpus* are resistant to Powdery Mildew whereas plants of 'Monlo' are susceptible to Powdery Mildew.
5. Leaves of plants of the new *Physocarpus* are burgundy in color whereas leaves of plants of 'Monlo' become green in color with development.

Plants of the new *Physocarpus* can be compared to plants of the *Physocarpus meyeri* 'Seward', disclosed in U.S. Plant Pat. No. 14,821. In side-by-side comparisons conducted in Grand Haven, Mich., plants of the new *Physocarpus* differed from plants of 'Seward' in the following characteristics:

1. Plants of the new *Physocarpus* were more compact and more upright than plants of 'Seward'.
2. Plants of the new *Physocarpus* had smaller leaves than plants of 'Seward'.
3. Plants of the new *Physocarpus* were not as freely flowering as plants of 'Seward'.

BRIEF DESCRIPTION OF THE PHOTOGRAPHS

The accompanying colored photographs illustrate the overall appearance of the new *Physocarpus,* showing the colors as true as it is reasonably possible to obtain in colored reproductions of this type. Colors in the photographs may differ slightly from the color values cited in the detailed botanical description which accurately describe the colors of the new *Physocarpus.*

The photograph at the bottom of the sheet is a side perspective view of a typical plant of 'Tres' grown in an outdoor nursery.

The photograph at the top of the sheet is a close-up view of typical inflorescences of 'Tres'.

DETAILED BOTANICAL DESCRIPTION

The aforementioned photographs and following observations, measurements and values describe plants grown in Grand Haven, Mich. during the spring and summer in an outdoor nursery and under conditions which closely approximate commercial production. Plants were five years old when the photographs and the description were taken. In the description, color references are made to The Royal Horticultural Society Colour Chart, 1995 Edition, except where general terms of ordinary dictionary significance are used.

Botanical classification: *Physocarpus opulifolius* 'Tres'.

Parentage:

*Female, or seed, parent.*—*Physocarpus opulifolius* 'Nana', not patented.

*Male, or pollen, parent.*—*Physocarpus opulifolius* 'Monlo', disclosed in U.S. Plant Pat. No. 11,211.

Propagation:

*Type.*—By softwood cuttings.

*Time to initiate roots.*—About 15 days at 25° C.

*Time to produce a rooted young plant.*—About 65 days at 25° C.

*Root description.*—Fine.

*Rooting habit.*—Freely branching; dense.

Plant description:

*Plant form and growth habit.*—Perennial shrub. Compact, upright and rounded plant habit; vigorous growth habit.

*Branching habit.*—Freely branching, about 502 lateral branches develop per plant; pinching enhances lateral branch development.

*Plant height.*—About 1.25 meters.

*Plant diameter* (*area of spread*).—About 1 meter.

Lateral branch description:

*Length.*—About 46 cm.

*Diameter.*—About 5 mm.

*Internode length.*—About 2.5 cm.

*Texture.*—Smooth, glabrous.

*Color.*—Close to 187A.

Foliage description:

*Arrangement.*—Alternate, simple.

*Length.*—About 4.5 cm.

*Width.*—About 5 cm.

*Shape.*—Ovate with lobing.

*Apex.*—Acute.

*Base.*—Truncate to obtuse.

*Margin.*—Crenate to dentate.

*Texture, upper and lower surfaces.*—Smooth, glabrous.

*Venation pattern.*—Pinnate.

*Color.*—Developing leaves, upper surface: Close to 187A. Developing leaves, lower surface: Close to 138A. Fully expanded leaves, upper surface: Close to 187A; venation, close to 187A. Fully expanded leaves, lower surface: Close to 191A; venation, close to 191A.

*Petiole.*—Length: About 2 cm. Diameter: About 1 mm. Texture, upper and lower surfaces: Smooth, glabrous. Color, upper and lower surfaces: Close to 187A.

Flower description:

*Flower appearance/arrangement.*—Single rotate flowers arranged in terminal and axillary corymbs; corymbs hemispherical in shape. Freely flowering habit with usually about 37 flowers per inflorescence. Flowers face upright to outwardly.

*Flower longevity.*—Flowers last for about two to three weeks on the plant; flowers last about one week as a cut flower; flowers not persistent.

*Natural flowering season.*—Plants flower from late May though early June in Grand Haven, Mich.

*Fragrance.*—Not detected.

*Inflorescence height.*—About 3 cm.

*Inflorescence diameter.*—About 3 cm.

*Flower diameter.*—About 8 mm.

*Flower length* (*height*).—About 6 mm.

*Flower bud.*—Length: About 3.5 mm. Diameter: About 3 mm. Shape: Elliptic. Color: Close to 65D.

*Petals.*—Arrangement/quantity: Single whorl of five petals. Length: About 4 mm. Width: About 4 mm. Shape: Elliptic to obovate. Apex: Obtuse. Margin: Entire. Texture, upper and lower surfaces: Smooth, glabrous. Color: When opening, upper surface: Close to 155D. When opening, lower surface: Close to 155D tinted with close to 65C. Fully opened, upper and lower surfaces: Close to 155D.

*Sepals.*—Arrangement/quantity: Single whorl of five petals. Length: About 3.5 mm. Width: About 3 mm. Shape: Broadly subulate. Apex: Acute. Margin: Entire. Texture, upper and lower surfaces: Smooth, glabrous. Color: When opening, upper and lower surfaces: Close to 144A. Fully opened, upper and lower surfaces: Close to 144A.

*Peduncles.*—Length: About 1.3 cm. Diameter: About 2 mm. Strength: Flexible. Texture: Smooth, glabrous. Color: Close to 144A.

*Pedicels.*—Length: About 2 cm. Diameter: About 1 mm. Strength: Flexible. Texture: Smooth, glabrous. Color: Close to 144A.

*Reproductive organs.*—Androecium: Quantity per flower: About 20 to 40. Anther shape: Oblong. Anther length: About 1.5 mm. Anther color: Close to 46A. Amount of pollen: Scarce. Pollen color: Close to 46A. Gynoecium: Quantity per flower: About three to four. Pistil length: About 0.5 mm. Style length: About 0.4 mm. Style color: Close to 145B. Stigma appearance: Globular. Stigma color: Close to 145B.

*Seeds/fruits.*—Seed and fruit development have not been observed on plants of the new *Physocarpus* plant.

Garden performance: Plants of the new *Physocarpus* have been observed to have good garden performance and to tolerate rain, wind and temperatures ranging from about −30° C. to about 37° C.

Pathogen/pest resistance: Plants of the new *Physocarpus* have been observed to be resistant to Powdery Mildew. Plants of the new *Physocarpus* have not been shown to be resistant to pests and other pathogens common to *Physocarpus.*

It is claimed:

1. A new and distinct *Physocarpus* plant named 'Tres' as illustrated and described.

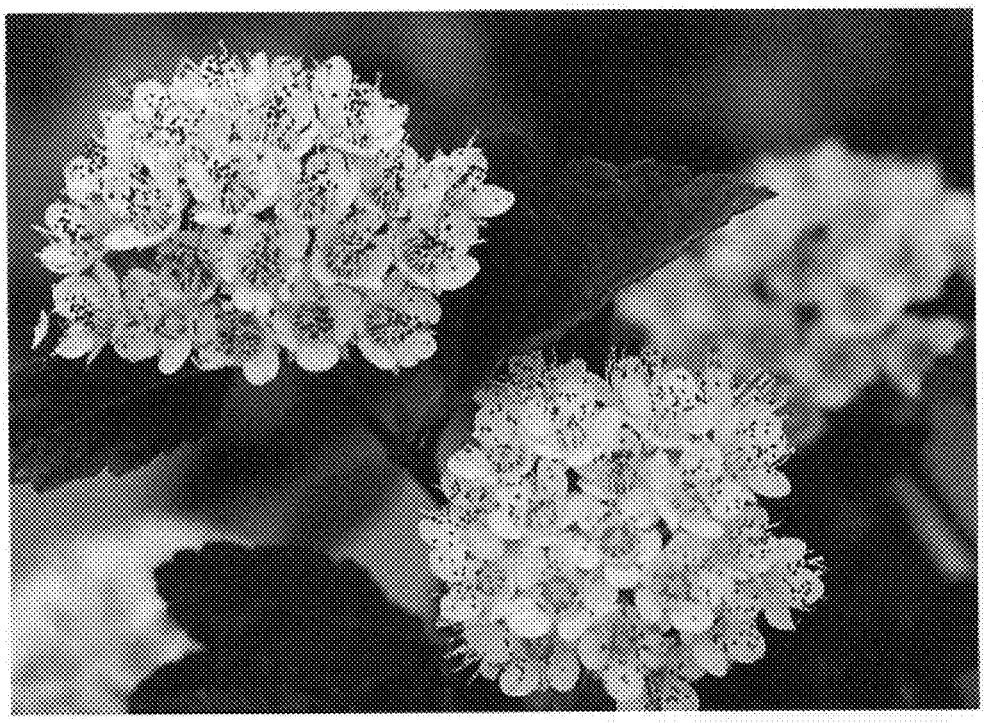
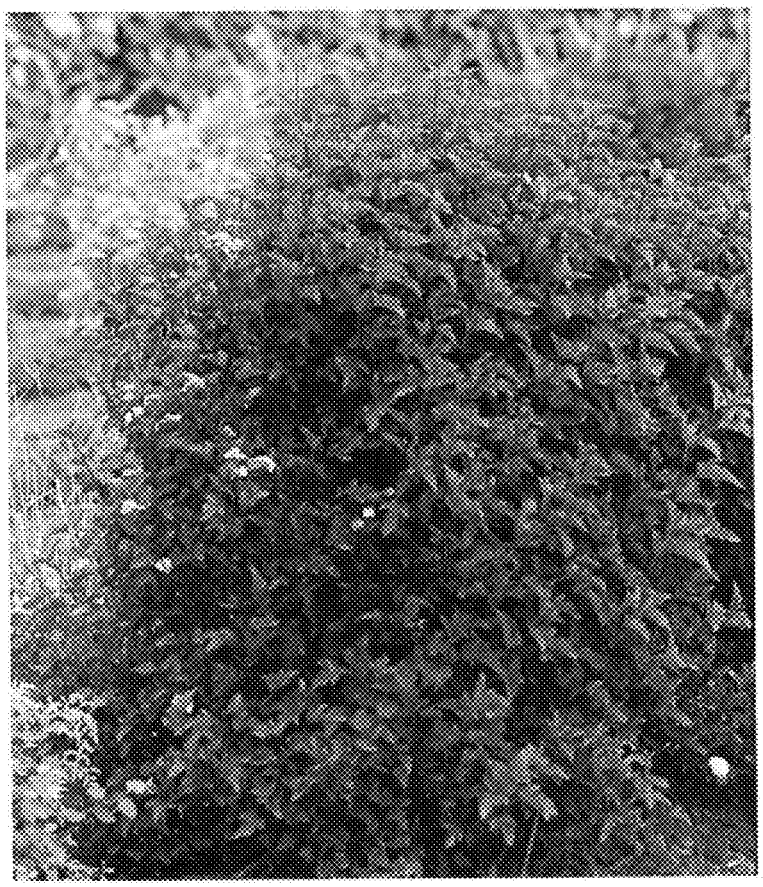

* * * * *